(12) United States Patent
Kurita et al.

(10) Patent No.: US 6,645,189 B2
(45) Date of Patent: Nov. 11, 2003

(54) DISPOSABLE PULL-ON DIAPER WITH DISPOSAL SECURING MEANS

(75) Inventors: Noriyuki Kurita, Kagawa-ken (JP); Tomoko Tsuji, Kagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/983,896

(22) Filed: Oct. 26, 2001

(65) Prior Publication Data

US 2002/0052593 A1 May 2, 2002

(30) Foreign Application Priority Data

Oct. 31, 2000 (JP) .......................................... 2000-332678

(51) Int. Cl.[7] .............................................. A61F 13/15
(52) U.S. Cl. ..................................... 604/385.13; 604/396
(58) Field of Search ........................ 604/385.01, 385.13, 604/385.16, 385.19, 385.201, 394–396, 385.24–385.3

(56) References Cited

U.S. PATENT DOCUMENTS 5,135,522 A * 8/1992 Fahrenkrug et al. ..... 604/385.3
5,531,732 A * 7/1996 Wood ......................... 604/391
6,402,731 B1 * 6/2002 Suprise et al. .............. 604/391

FOREIGN PATENT DOCUMENTS

| JP | 1998-71172 | 3/1998 |
| JP | 1998-71173 | 3/1998 |
| JP | 1998-85254 | 4/1998 |

* cited by examiner

Primary Examiner—Weilun Lo
Assistant Examiner—C Lynne Anderson
(74) Attorney, Agent, or Firm—Lowe Hautpman Gilman & Berner LLP

(57) ABSTRACT

A disposable pull-on diaper has a disposal securing means. This means includes perforated lines which are formed between transversely opposite side edges of front and rear waist regions and respective first joining zones, along which top- and backsheets are torn together to define slits. The perforated lines extend in a longitudinal direction between the vicinity of a peripheral edge portion of a waist-opening and the vicinity of peripheral edge portions of respective leg-openings.

8 Claims, 5 Drawing Sheets

DISPOSABLE PULL-ON DIAPER WITH DISPOSAL SECURING MEANS

BACKGROUND OF THE INVENTION

This invention relates to a disposable pull-on diaper adapted to be secure in rolled up state for disposal after use.

It is well known in the art to provide a disposable pull-on diaper with tape fasteners by which the diaper may be secured in rolled up state for disposal after use. For disposal, the diaper is rolled up in the longitudinal direction starting from the crotch region toward the peripheral edge portion of the waist-opening or vice versa and then the tape fasteners are wound around the outer surface of such rolled up diaper to secure the diaper in this rolled up state. The tape fastener is made of flexible plastic sheet coated on its inner surface with pressure-sensitive adhesive by means of which the tape fastener is anchored on the outer surface of the diaper.

The disposable pull-on diaper provided with such tape fasteners is well known, for example, from Japanese Patent Application Publication Nos. 1998-71172A, 1998-71173A and 1998-85254A.

Use of the tape fasteners to secure the diaper in rolled up state is advantageous in that the handling for disposal is conveniently simplified. However, use of the tape fasteners has drawbacks that the tape fasteners inevitably have stiffness higher than that of any other components constituting the diaper, e.g., the top- and backsheets as well as the liquid-absorbent core and, in addition, the wearer may experience uncomfortable irritation should the wearer's skin come in contact with the tape fasteners during use of the diaper. Furthermore, once the pressure-sensitive adhesive surface has been fouled, the tape fasteners will lose its initial bonding property and no more useful.

SUMMARY OF THE INVENTION

It is an object of this invention to provide a disposable pull-on diaper improved so that the diaper can be secured in rolled up state for disposal without use of the so-called tape fasteners.

According to this invention, there is provided a disposable pull-on diaper comprising a liquid-pervious topsheet, a liquid-impervious backsheet and a liquid-absorbent core disposed between these two sheets to constitute a front waist region, a rear waist region opposed to said front waist region and a crotch region positioned between these two waist regions wherein said front and rear waist regions are joined together along first joining zones extending in a longitudinal direction in the vicinity of transversely opposite side edges of said front and rear waist regions to define a waist-opening and a pair of leg-openings.

The pants-type disposable diaper further comprises a pair of slits being defined between the transversely opposite side edges and said first joining zones, by tearing said topsheet and said backsheet, the slits extending in said longitudinal direction between the vicinity of a peripheral edge portion and the vicinity of peripheral edge portions of said leg-openings so that a pair of ribbon-like portions which extend in said longitudinal direction being formed between said slits and the transversely opposite side edges of said front and rear waist regions.

According to one preferred embodiment of this invention, perforated lines serving to tear said top- and backsheets are defined between the transversely opposite side edges of said front and rear waist regions and said first joining zones, respectively, and extend in said longitudinal direction between the vicinity of said peripheral edge portion of said waist-opening and the vicinity of said peripheral edge portions of said leg-openings so that said top- and backsheets may be torn along said perforated lines to define said slits.

According to another preferred embodiment of this invention, said ribbon-like portions are formed in second joining zones extending in said longitudinal direction.

DETAILED DESCRIPTION OF THE INVENTION

Details of a disposable pull-on diaper according to this invention will be more fully understood from the description given hereunder with reference to the accompanying drawings.

Figure 1:
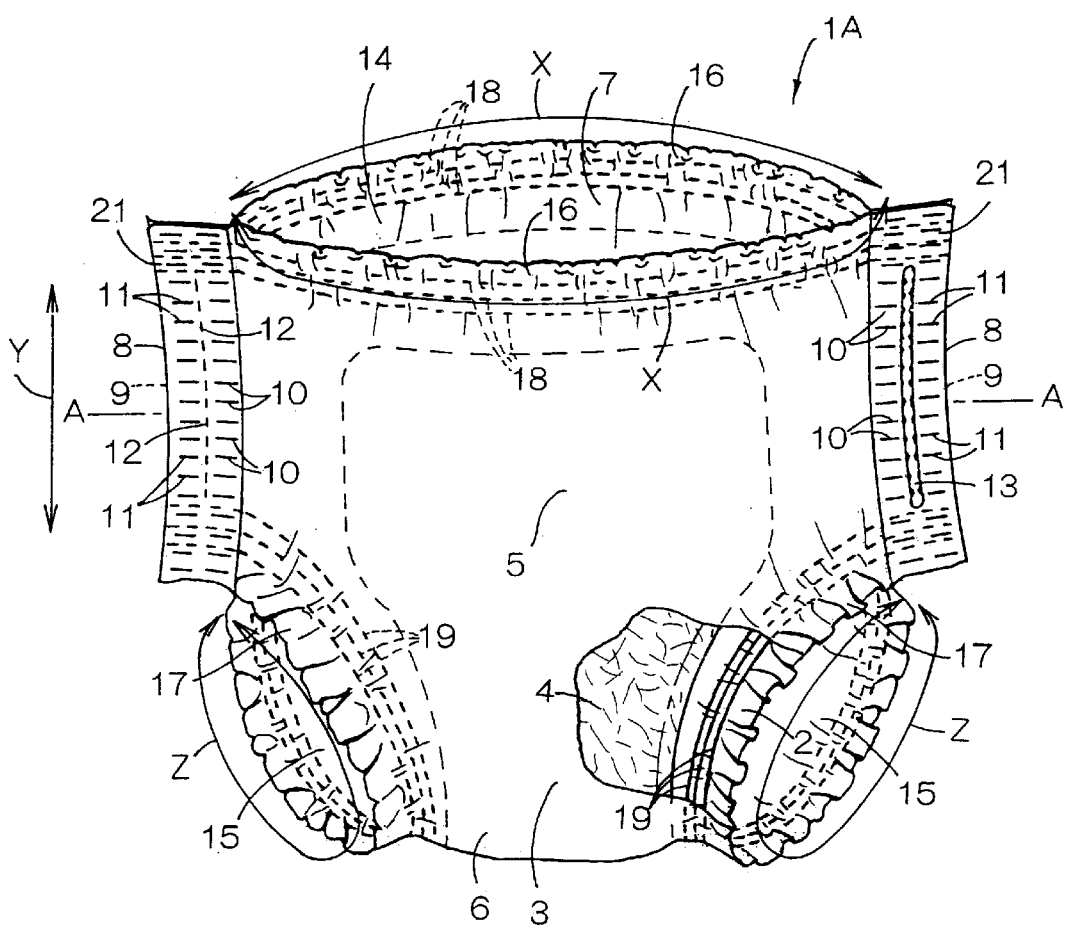
FIG. 1 is a perspective view showing a partially cutaway disposable pull-on diaper as viewed from the front waist region.
Figure 2:
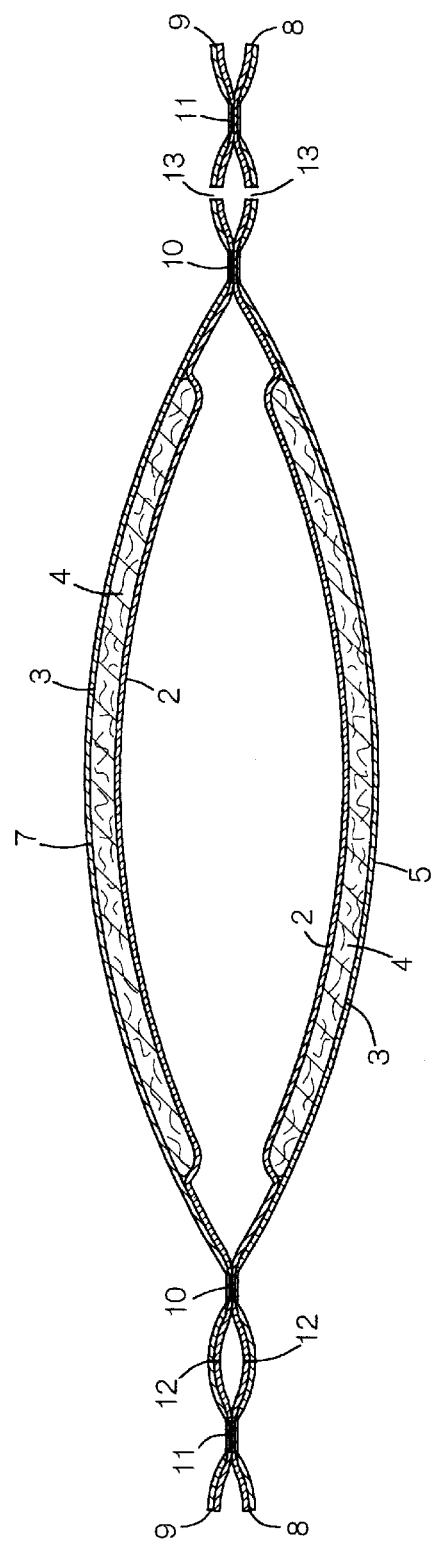
FIG. 2 is a sectional view taken along a line A—A in FIG. 1.

FIG. 1 is a perspective view showing a partially cutaway disposable pull-on diaper 1A as viewed from the side of a front waist region 5 and FIG. 2 is a sectional view taken along a line A—A in FIG. 1. FIG. 1 shows the diaper 1A having top- and backsheets 2, 3 partially torn along each of perforated lines 12, providing in the vicinity of transversely opposite side edges 8, 9 so as to define a slit 13 extending in a longitudinal direction. Referring to FIG. 1, a waist-surrounding direction is indicated by an arrow X, a longitudinal direction is indicated by an arrow Y1 and a leg-surrounding direction is indicated by an arrow Z. Surfaces of the top- and backsheets 2, 3 which face a core 4 will be referred to herein as "inner surfaces" and surfaces of these sheets 2, 3 which do not face the core 4 will be referred to herein as "outer surfaces".

The diaper 1A basically comprises the liquid-pervious topsheet 2, the liquid-impervious backsheet 3 and the liquid-absorbent core 4 disposed between these sheets 2, 3 and entirely covered with and joined to a liquid-diffusion layer formed of materials such as tissue paper (not shown). The core 4 is joined to the inner surfaces of the top- and backsheets 2, 3 with the liquid-diffusion layer therebetween.

The diaper 1A is composed of front and rear waist regions 5, 7 opposed to each other and a crotch region 6 positioned between these waist regions 5, 7. The front and rear waist regions 5, 7 are overlapped and joined together in the vicinity of the transversely opposite side edges 8, 9 thereof by means of a plurality of first joining zones 10 arranged intermittently in the longitudinal direction. Thereby the diaper 1A is formed with a waist-opening 14 and a pair of leg-openings 15.

Between the transversely opposite side edges 8, 9 of the front and rear waist regions 5, 7 and the respective first joining zones 10, a plurality of second joining zones 11 arranged intermittently in the longitudinal direction. In the first and second joining zones 10, 11, the topsheet 2 is joined to each other with its inner surface overlaid, and the top- and backsheets 2, 3 are joined to each other. Bonding of these sheets 2, 3 is carried out using a heat-welding technique.

Between the first joining zones 10 and the associated second joining zones 11, the perforated lines 12 are formed which respectively extend in the longitudinal direction between the vicinity of a peripheral edge portion 16 of the waist-opening 14 and the vicinity of peripheral edge portions 17 of the respective leg-openings 15. For the diaper 1A, it is possible to tear the top- and backsheets 2, 3 together along the perforated lines 12 and thereby defining the slits 13 extending in the longitudinal direction between the first joining zones 10 and the associated second joining zones 11 as shown in FIG. 1.

Along a peripheral edge portion 16 of the waist-opening 14, an elastic member 18 composed of a plurality of elastic elements extensible in the waist-surrounding direction is disposed between the top- and backsheets 2, 3 and bonded under tension to the inner surfaces of these sheets 2, 3. Along a peripheral edge portion 17 of each of leg-openings 15, an elastic member 19 composed of a plurality of elastic elements extensible in a leg-surrounding direction is disposed between the top- and backsheets 2, 3 and joined under tension to the inner surfaces of the sheets 2, 3. Referring to FIG. 1, a plurality of gathers are formed along the peripheral edge portion 16 of the waist-opening 14 and the peripheral edge portion 17 of the leg-openings 15 as the elastic members 18, 19 contract themselves.

Figure 3:
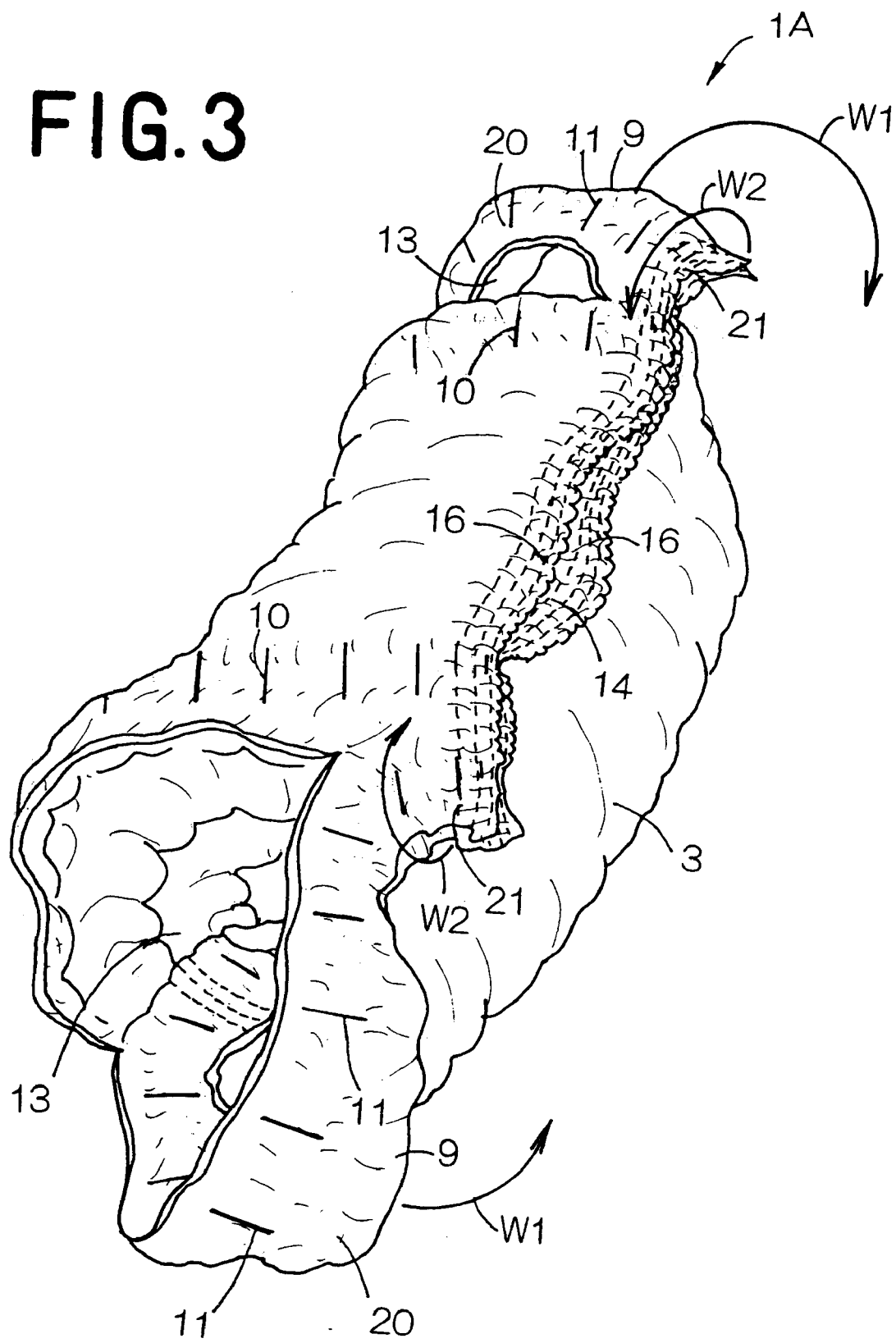
FIG. 3 is a perspective view showing the diaper of FIG. 1 as having been rolled up for disposal.
Figure 4:
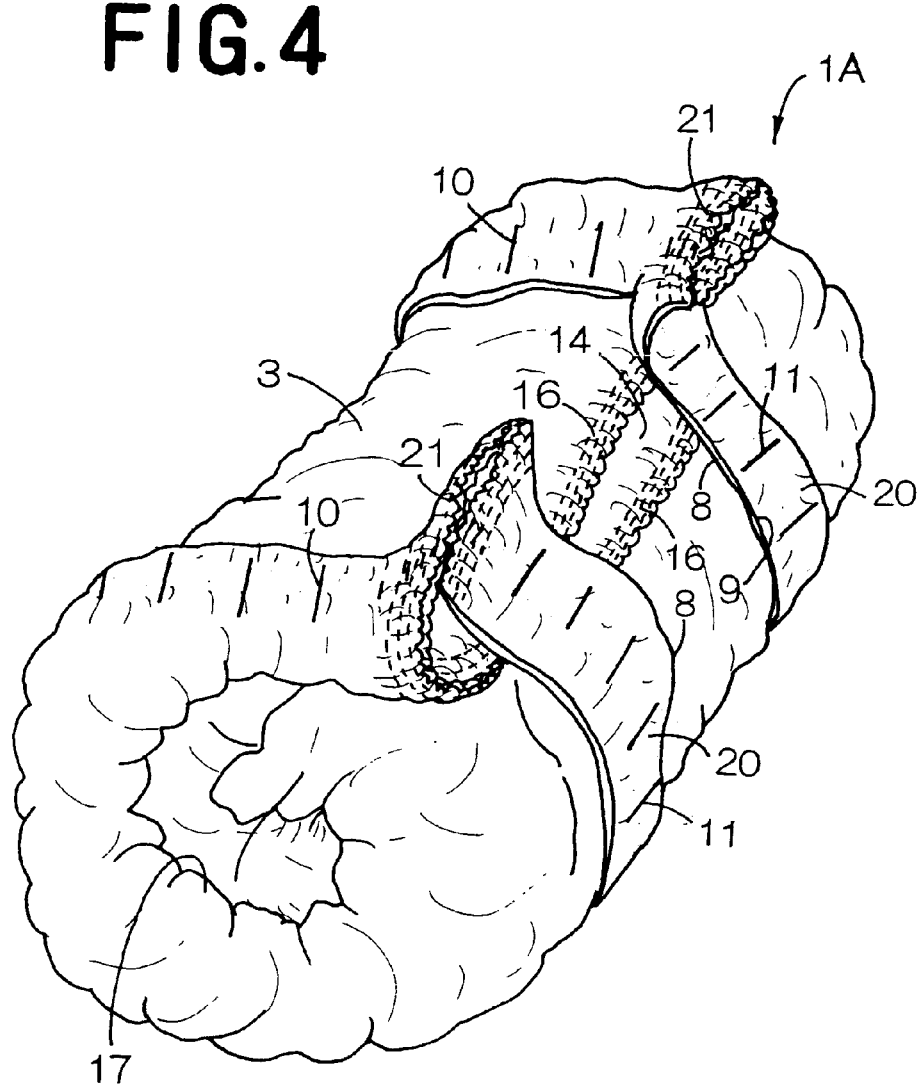
FIG. 4 is a perspective view showing the diaper of FIG. 1 as having been rolled up for disposal.

FIGS. 3 and 4 are perspective views showing the diaper 1A of FIG. 1 as having been rolled up for its disposal. In FIGS. 3 and 4, the diaper 1A has been rolled up in the longitudinal direction starting from the crotch region 6 toward the peripheral edge portion 16 of the waist-opening 14 with the front waist region 5 inside. FIG. 3 shows the state of the state of the rolled up diaper 1A before the ribbon-like portions 20 defined between the transversely opposite side edges 8, 9 and the adjacent slits 13 are wound around the outer surface of the rolled up diaper 1A.

Tearing the top- and backsheets 2, 3 along the perforated line 12 provides the slits 13 extending in the longitudinal direction in the vicinity of its transversely opposite side edges 8, 9 of the diaper 1A and at the same time forms a pair of the ribbon-like portions 20 extending in the longitudinal direction between the transversely opposite side edges 8, 9 of the front and rear waist regions 5, 7.

For disposal of this diaper 1A, the diaper 1A is rolled up starting from the crotch region 6 toward the peripheral edge portion 16 of the waist-opening 14 with the front waist region 5 inside. Then, the ribbon-like portions 20 are moved in a direction indicated by an arrow W1, the corners 21 at which the peripheral edge portion 16 intersects the transversely opposite side edges 8, 9 are folded back in a direction indicated by an arrow W2 and the respective ribbon-like portions 20 are wound around the outer surface of the rolled up diaper 1A, as shown by FIG. 3.

Thus the diaper 1A is held by the respective ribbon-like portions 20 in its rolled up state. A pair of ribbon-like portions 20 are wrapped around the peripheral edge portion 16 of the waist-opening 14 and the peripheral edge portions 17 of the leg-openings 15 are rolled up together with the diaper 1A. Consequently, it is not likely that the waist-opening 14 and the leg-openings 15 might be unintentionally opened and excretion and/or its odor might leak from these openings.

This diaper 1A allows itself to be held in rolled up state without use of the so-called tape fasteners. The absence of the tape fasteners advantageously avoids uncomfortable stimulus which otherwise might be experienced by a wearer due to contact with the tape fasteners during use of the diaper 1A.

The ribbon-like portions 20 including the second joining zones 11 arranged intermittently in the longitudinal direction, so there is no anxiety that the top- and backsheets 2, 3 in the respective ribbon-like portions 20 might be separated from each other and these ribbon-like portions 20 can be easily wound around the outer surface of the rolled up diaper 1A. It should be understood that it is not essential for this diaper 1A to provide the second joining zones 11.

For disposal of this diaper 1A, it is also possible to roll up the diaper starting from the peripheral edge portion 16 of the waist-opening 14 toward the crotch region 6 in the longitudinal direction and then to wind the ribbon-like portions 20 around the outer surface of the rolled up diaper 1A. With the diaper 1A rolled up in this manner, the peripheral edge portion 16 of the waist-opening 14 is confined within the rolled up diaper 1A and there is no possibility that the waist-opening 14 might be exposed to the outer surface of the rolled up diaper 1A.

Figure 5:
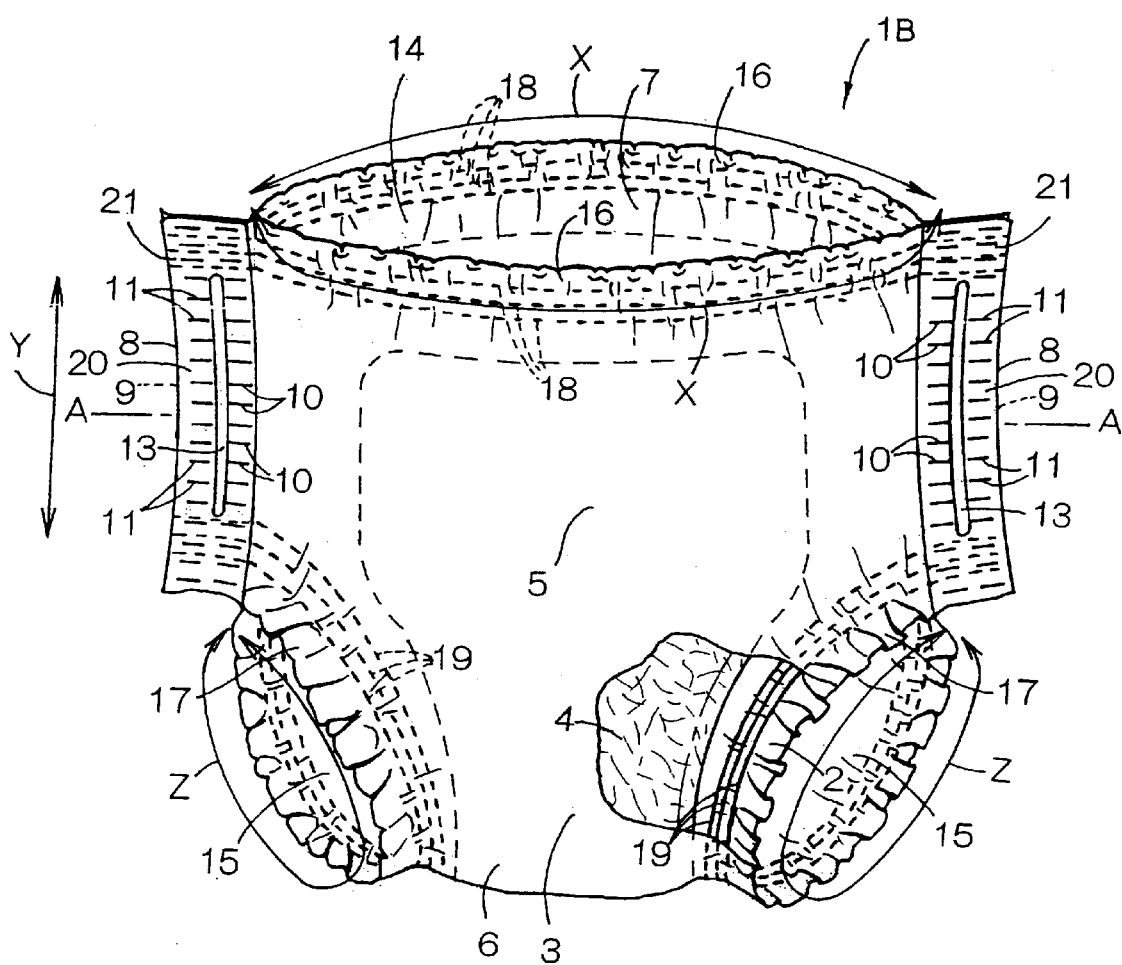
FIG. 5 is a perspective view showing the partially cutaway diaper according to the embodiment different from FIG. 1 as viewed from the side of the front waist region.

FIG. 5 is a perspective view showing a partially cutaway disposable diaper 1B according to an embodiment different from FIG. 1 as viewed from the side of the front waist region 5. This diaper 1B is different from the diaper 1A of FIG. 1 in the arrangement as follows: Between each pair of the adjacent first and second joining zones 10, 11, the slit 13 is formed, which extends in the longitudinal direction from the vicinity of the peripheral edge portion 16 of the waist-opening 14 to the vicinity of the peripheral edge portion 17 of the leg-opening 15. Each of such slits 13 is defined by partially tearing the top- and backsheets 2, 3 together.

Also in the case of this diaper 1B, a pair of the ribbon-like portions 20 extending in the longitudinal direction are formed between the transversely opposite side edges 8, 9 and the associated slits 13, respectively. For disposal of the diaper 1B, the diaper 1B is rolled up starting from the crotch region 6 toward the peripheral edge portion 16 of the waist-opening 14 with the front waist region 5 inside and the ribbon-like portions 20 are wound around the outer surface of the rolled up diaper 1B similarly to the case of the diaper 1A shown in FIG. 1.

The topsheet 2 may be formed of a hydrophilic fibrous nonwoven fabric or a porous plastic film. The backsheet 3 may be formed of a hydrophobic fibrous nonwoven fabric, a liquid-impervious plastic film or a laminated composite sheet of hydrophobic nonwoven fabric and plastic film. The backsheet 3 may be also formed of a composite nonwoven fabric consisting of a melt blown fibrous nonwoven fabric having a high water-resistant property sandwiched by two layers of spun bond nonwoven fabric having high strength and flexibility.

The nonwoven fabric may be selected from a group including spun lace-, needle punch-, melt blown-, thermal bond-, spun bond-, chemical bond- and air through-nonwoven fabrics. Component fibers of the nonwoven fabric may be selected from a group including polyolefine-, polyester- and polyamide-based fibers and polyethylene/polypropylene or polyethylene/polyester core-sheath type conjugated fibers and side-by-side-type conjugated fibers.

The core 4 is a mixture of fluff pulp, high absorption polymer particles and thermoplastic synthetic resin fibers compressed to a desired thickness. The polymer particles may be selected from a group including starch-, cellulose-based polymer and synthetic polymer.

To join the top- and backsheets 2, 3 to each other, to bond the core 4 to the top- and backsheets 2, 3 and to attach the elastic members 19, 20 to the diaper, suitable adhesives such as hot melt adhesives or welding means such as heat-sealing or ultrasonic sealing well known in the art may be used.

The disposable pull-on diaper according to this invention can be held in rolled up state by winding the ribbon-like portions formed between the transversely opposite side edges of the front and rear waist regions around the outer surface of the rolled up diaper. Use of the so-called tape fasteners is not required by this diaper, so the wearer is free from uncomfortable irritation experienced during use of the diaper due to contact with the tape fasteners as the conventional diaper provided with the tape fasteners has been the case.

With the diaper having been rolled up and fastened by the ribbon-like portions wound therearound, these two ribbon-like portions extend across the peripheral edge portion of the waist-opening and the peripheral edge portions of the respective leg-openings are confined within the rolled up diaper. Consequently, there is no anxiety that the waist-opening and the leg-openings might be unintentionally opened and excretion and/or its odor might leak from these openings.

In the case of the diaper adapted to define the slits upon tearing the top- and backsheets along the perforated lines, the ribbon-like portions are formed for the first time when disposal of the diaper is intended. In this way, it is not likely that the ribbon-like portions might independently move during use of the diaper and obstruct proper wearing of the diaper as such inconvenience has often occurred in the diaper previously formed with the slits.

What is claimed is:

1. A pants-type disposable diaper, comprising a liquid-pervious topsheet, a liquid-impervious backsheet and a liquid-absorbent core disposed between said topsheet and said backsheet to define a front waist region, a rear waist region opposed to said front waist region and a crotch region positioned between said front waist region and said rear waist region, wherein said front waist region and said rear waist region are joined together along first joining zones extending in a longitudinal direction in the vicinity of transversely opposite side edges of said front waist region and said rear waist region to define a waist-opening and a pair of leg-openings;

said diaper further comprising a pair of slits that are respectively located between the transversely opposite side edges and said first joining zones, said slits extending through said topsheet and said backsheet, said slits extending in said longitudinal direction between the vicinity of a peripheral edge portion of said waist opening and the vicinity of peripheral edge portions of said leg-openings to define a pair of ribbon portions, which extend in said longitudinal direction, between said slits and the transversely opposite side edges.

2. The diaper according to claim 1, wherein the topsheet and backsheet, in said ribbon portions, are joined together along second joining zones extending in said longitudinal direction.

3. The diaper according to claim 1, wherein said diaper consists essentially of said liquid-pervious topsheet, said liquid-impervious backsheet, said liquid-absorbent core and said slits.

4. The diaper according to claim 1, wherein a longitudinal extent of each of said slits in said longitudinal direction is about half a circumferential dimension of said diaper when said diaper is in a rolled state.

5. The diaper according to claim 1, wherein a longitudinal extent of each of said perforated lines in said longitudinal direction is about half a circumferential dimension of said diaper when said diaper is in a rolled state.

6. A pants-type disposable diaper, comprising a liquid-pervious topsheet, a liquid-impervious backsheet and a liquid-absorbent core disposed between said topsheet and said backsheet to define a front waist region, a rear waist region opposed to said front waist region and a crotch region positioned between said front waist region and said rear waist region, wherein said front waist region and said rear waist region are joined together along first joining zones extending in a longitudinal direction in the vicinity of transversely opposite side edges of said front waist region and said rear waist region to define a waist-opening and a pair of leg-openings;

said diaper further comprising a pair of perforated lines along which the topsheet and the backsheet are perforated, said perforated lines being respectively located between the transversely opposite side edges and said first joining zones, said perforated lines extending in said longitudinal direction between the vicinity of a peripheral edge portion of said waist-opening and the vicinity of peripheral edge portions of said leg-openings, thereby allowing topsheet and backsheet to be torn along said perforated lines to form a pair of slits.

7. The diaper according to claim 6, wherein the topsheet and backsheet, in an area between each of said perforated lines and the respective one of said transversely opposite side edges, are joined together along second joining zones extending in said longitudinal direction.

8. The diaper according to claim 6, wherein said diaper consists essentially of said liquid-pervious topsheet, said liquid-impervious backsheet, said liquid-absorbent core and said perforated lines.

* * * * *